（12）United States Patent
Kaiser et al.

(10) Patent No.: US 10,716,496 B2
(45) Date of Patent: Jul. 21, 2020

(54) DETERMINATION OF BREATHING SIGNAL FROM THERMAL IMAGES

(71) Applicant: Brainlab AG, Munich (DE)

(72) Inventors: Hagen Kaiser, Munich (DE); Kajetan Berlinger, Munich (DE)

(73) Assignee: BRAINLAB AG, Munich (DE)

( * ) Notice: Subject to any disclaimer, the term of this patent is extended or adjusted under 35 U.S.C. 154(b) by 457 days.

(21) Appl. No.: 15/527,651

(22) PCT Filed: Apr. 28, 2015

(86) PCT No.: PCT/EP2015/059171
§ 371 (c)(1),
(2) Date: May 17, 2017

(87) PCT Pub. No.: WO2016/087058
PCT Pub. Date: Jun. 9, 2016

(65) Prior Publication Data
US 2017/0354330 A1    Dec. 14, 2017

Related U.S. Application Data

(63) Continuation-in-part of application No. PCT/EP2014/076287, filed on Dec. 2, 2014.

(51) Int. Cl.
*A61B 5/00*     (2006.01)
*A61B 5/113*    (2006.01)
(Continued)

(52) U.S. Cl.
CPC .......... *A61B 5/1128* (2013.01); *A61B 5/0035* (2013.01); *A61B 5/0064* (2013.01);
(Continued)

(58) Field of Classification Search
CPC ..... A61B 5/0077; A61B 5/113; A61B 5/7292; A61B 5/015; A61B 2090/371;
(Continued)

(56) References Cited

U.S. PATENT DOCUMENTS

| | | | |
|---|---|---|---|
| 6,937,696 B1 * | 8/2005 | Mostafavi | A61B 5/113 378/65 |
| 2009/0082687 A1 * | 3/2009 | Onishi | A61B 5/0803 600/534 |

(Continued)

FOREIGN PATENT DOCUMENTS

| | | |
|---|---|---|
| CN | 2376865 Y | 5/2000 |
| CN | 2688223 Y | 3/2005 |

(Continued)

OTHER PUBLICATIONS

Noonan et al., Accurate Markerless Respiratory Tracking for Gated Whole Body PET Using the Microsoft Kinect, 2012 (Year: 2012).*

(Continued)

*Primary Examiner* — Joanne M Hoffman
*Assistant Examiner* — Alexei Bykhovski
(74) *Attorney, Agent, or Firm* — Middleton Reutlinger

(57) ABSTRACT

A data processing method performed by a computer for determining breathing signal data which represents a breathing cycle of a patient, comprising the steps of: —acquiring image data representing a sequence of training thermal images of at least a part of the surface of the patient's body over time, the sequence covering at least one half breathing cycle and being captured by a thermographic camera; and —tracking at least one tracked point in the image data over the sequence of training thermal images to find a trajectory of the tracked point as the breathing signal data, wherein the tracked point is a point on the surface of the patient's body.

14 Claims, 7 Drawing Sheets

(51) Int. Cl.
  A61B 5/01    (2006.01)
  A61B 5/11    (2006.01)
  H04N 13/204  (2018.01)
  A61N 5/10    (2006.01)
  G01J 5/00    (2006.01)
  G03B 35/02   (2006.01)
  G06T 7/33    (2017.01)
  G06T 7/70    (2017.01)
  A61B 5/055   (2006.01)
  A61B 6/03    (2006.01)
  A61B 6/00    (2006.01)
  G06T 7/00    (2017.01)
  H04N 13/00   (2018.01)
  H04N 13/239  (2018.01)
  G01J 5/10    (2006.01)
  G01R 33/48   (2006.01)

(52) U.S. Cl.
  CPC .......... *A61B 5/0077* (2013.01); *A61B 5/015* (2013.01); *A61B 5/055* (2013.01); *A61B 5/11* (2013.01); *A61B 5/113* (2013.01); *A61B 5/7292* (2013.01); *A61B 6/032* (2013.01); *A61B 6/5247* (2013.01); *A61N 5/1049* (2013.01); *A61N 5/1068* (2013.01); *G01J 5/00* (2013.01); *G03B 35/02* (2013.01); *G06T 7/0012* (2013.01); *G06T 7/33* (2017.01); *G06T 7/70* (2017.01); *H04N 13/204* (2018.05); *A61B 2560/0223* (2013.01); *A61B 2576/00* (2013.01); *A61B 2576/02* (2013.01); *A61N 5/1069* (2013.01); *G01J 5/10* (2013.01); *G01J 2005/0077* (2013.01); *G01J 2005/0081* (2013.01); *G01R 33/4808* (2013.01); *G06T 2207/10004* (2013.01); *G06T 2207/10028* (2013.01); *G06T 2207/10048* (2013.01); *G06T 2207/10081* (2013.01); *G06T 2207/10088* (2013.01); *G06T 2207/30196* (2013.01); *H04N 13/239* (2018.05); *H04N 2013/0081* (2013.01)

(58) Field of Classification Search
  CPC ..... A61B 5/055; A61B 5/1127; A61B 5/7289; A61B 6/463; A61B 6/5288; A61B 6/541; A61B 90/39; A61N 5/1049; A61N 5/1068; A61N 2005/1059; A61N 5/1037; A61N 5/1048; A61N 5/1064
  See application file for complete search history.

(56) References Cited

U.S. PATENT DOCUMENTS

| | | | |
|---|---|---|---|
| 2010/0284592 A1* | 11/2010 | Arnon | A61B 5/015 382/128 |
| 2012/0226152 A1 | 9/2012 | Fatih | |
| 2012/0289850 A1 | 11/2012 | Xu et al. | |
| 2013/0342691 A1 | 12/2013 | Lewis et al. | |
| 2014/0236036 A1 | 8/2014 | de Haan et al. | |

FOREIGN PATENT DOCUMENTS

| | | |
|---|---|---|
| CN | 201905863 U | 7/2011 |
| CN | 102973273 A | 3/2013 |
| DE | 102011079264 A1 | 1/2013 |
| GB | 2418495 A | 3/2006 |
| JP | 2002528194 A | 9/2002 |
| JP | 2011500263 A | 1/2011 |
| TW | 201249405 A | 12/2012 |
| WO | WO2014/048490 A1 | 4/2014 |
| WO | WO2016/087058 A1 | 6/2016 |

OTHER PUBLICATIONS

Langer et al., Prospective displacement and velocity-based cine 4D CT, Sep. 2008 (Year: 2008).*
Japanese Patent Office; Office Action issued in Application No. 2017-529759 dated Apr. 18, 2018.
Wasza, et al. "Real-time motion compensated patient positioning and non-rigid deformation estimation using 4-d shape priors". Lecture Notes in Computer Science, Springer vol. 7511, 2012, pp. 576-583.
Calonder, et al. "BRIEF: Computing a local binary descriptor very fast."
International Search Report and Written Opinion, PCT/EP2015/059171, dated Sep. 6, 2016.
European Patent Office; Communication issued in Application No. 15 717 927.6 dated Dec. 5, 2018.

* cited by examiner

DETERMINATION OF BREATHING SIGNAL FROM THERMAL IMAGES

The present invention relates to a data processing method, performed by a computer, for determining breathing signal data which represents a breathing cycle of a patient and to a corresponding computer program and system.

Many medical applications benefit from knowing a breathing signal of a patient, or even require the breathing signal. A typical application is radiotherapy or radiosurgery, wherein a treatment beam is gated or guided in accordance with the breathing signal. The breathing typically occurs in a periodic cycle. This document thus relates to determining breathing signal data which represents a breathing cycle of a patient.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a data processing method performed by a computer for determining breathing signal data which represents a breathing cycle of a patient. The method comprises the step of acquiring image data representing a sequence of training thermal images of at least a part of the surface of the patient's body over time, the sequence covering at least one half breathing cycle and being captured by a thermographic camera. The method further comprises the step of tracking at least one tracked point in the image data over the sequence of training thermal images to find a trajectory of the tracked point as the breathing signal data, wherein the tracked point is a point on the surface of the patient's body. The tracked point can also be referred to as a thermal landmark.

The part of the surface of the patient's body which is shown in the thermal images is preferably a part which moves when the patient breathes. This means that a point in this area of the surface moves as the patient breathes, such that the position at which this point is imaged in the images of the sequence of training thermal images changes over time. For the sake of brevity, this position is also referred to as position of the tracked point or position of the tracked point in a thermal image.

While it might be sufficient if the sequence of training thermal images covers one half breathing cycle, the sequence preferably covers a full breathing cycle or even more.

Tracking the point in the image data means to determine the position of the tracked point in the sequence of training thermal images. The result of the tracking step is a sequence of positions of the tracked point, which represent discrete samples of the trajectory of the tracked point. The trajectory is represented by this set of positions or can be a closed curve which is defined by the positions, and can for example be obtained by fitting a curve in to the positions of the tracked point, thus obtaining a best-fit curve. The trajectory does not only have a particular shape, but also has temporal aspect because it is traversed once during full breathing cycle. It typically is a two-dimensional curve in the co-ordinate system of the thermal images.

The thermographic camera is preferably fixed in space. The position of the tracked point in the sequence of training thermal images is therefore defined by the movement of the tracked point in space. If the patient does not move in space, the movement of the tracked point in space is solely caused by the breathing activity of the patient.

The word "training" in the expression "training thermal images" means that the training thermal images are used for determining the trajectory of the tracked point, which is a kind of training process for the method. Optional subsequent steps of the method make use of live thermal images, which are images captured by the thermographic camera after the training thermal images were captured.

In a typical case, the trajectory has an oval shape. The trajectory then has two major vertices, which are the two points on the trajectory which are most distant from each other. In typical cases, those two major vertices define the point at which the inhale portion of the breathing cycle stops and turns into the exhale portion or vice versa.

An aspect of the present invention is to derive the breathing signal from a temporal sequence of two-dimensional thermal images. In a thermal image, the pixels do not represent the colour of a point in the visible spectrum, but rather a temperature or temperature distribution emitted from the point. Since each point emits a range of temperatures up to a maximum temperature, a pixel of a thermal image can for example represent this maximum temperature of the point. In this document, a thermal image preferably only represents the thermal radiation emitted from the surface of the patient's body in a non-visible spectrum. A thermal image can only be effectively presented to a human eye if frequency mapping is performed. This is often referred to as false-colour representation.

The advantage of using thermal images is that the spectrum of the thermal radiation is independent of ambient conditions, such as illumination, and the optical properties of the surface, so even if a large area of the surface has the same optical properties in the visual spectrum, it may exhibit a particular pattern in its thermal radiation, such that a point on the surface of the patient can be reliably identified and tracked in the sequence of thermal images.

In one embodiment, the thermal two-dimensional images represent wavelengths between 8 μm and 14 μm. This range corresponds to typical temperatures for the surface of a patient's body. The thermal two-dimensional images preferably do not represent wavelengths in the near infrared spectrum. The near infrared spectrum is typically understood to extend as far as wavelengths of 2.5 μm or 3 μm.

In one embodiment, the method further comprises the steps of defining a gating region in a live thermal image captured by the thermographic camera, finding the position of the tracked point in the live thermal image and generating a gating signal indicating whether or not the tracked point is within the gating region. As outlined above, a live thermal image is an image which is captured after the training thermal images were captured and represents a current state of the patient. The gating region is for example an area of the live thermal image, such as for example a rectangular area. The gating region can for example be set automatically, for example so as to comprise a vertex of the trajectory, or be input by a user.

If the position of the tracked point lies within the gating region, this means that the patient is in a particular part of the breathing cycle. This means at the same time that a structure, such as for example a tumour, is in a particular position, such that a treatment beam can be activated. The gating region is for example a region in which one of the major vertices of the trajectory lies. Since this point typically represents the transition from inhale to exhale or vice versa, this means that the object does not move, or moves only very little, at the times at which the position of the tracked point is within the gating region. The gating signal can be used for turning a treatment beam on and off as it is known in the art.

This embodiment provides a simple approach with little computational complexity for determining a gating signal for controlling a treatment beam by suitably defining the gating region in the live thermal image.

In one embodiment, the method further comprises the steps of defining a corridor around the trajectory in a live thermal image captured by the thermographic camera, finding the position of the tracked point in the live thermal image and outputting a movement warning signal if the position of the tracked point is outside the corridor.

As outlined above, the thermographic camera is preferably fixed in space. The position of the tracked point in a live thermal image is therefore defined by a superposition of the breathing movement and an additional movement of the patient. The additional movement might be caused by coughing or any other intentional or unintentional movement. If the tracked point is outside the corridor, it is assumed that an additional movement has occurred. This means that the patient is most likely no longer in a desired position, such that it might be beneficial to stop a medical treatment, such as radiosurgery or radiotherapy. This embodiment therefore allows for outputting a warning if an undesired movement of the patient occurs, such that the patient is no longer in a desired position.

In this embodiment, the expression "corridor" means an area which surrounds the trajectory to the left and to the right. The corridor is for example defined by a number of pixels to the left of the trajectory and a number of pixels to the right of the trajectory. The expressions "to the left" and "to the right" are defined with respect to the direction in which the trajectory is traversed and preferably relate to directions orthogonal to the trajectory.

Instead of defining a corridor, which broadens the trajectory, an area can be defined which surrounds the complete trajectory. This area can for example have an oval shape or a rectangular shape. The movement warning signal is then output if the tracked point is outside the area. This further reduces the computational complexity.

In one embodiment, the position of the patient in space is ascertained if a movement warning signal has been output. The moving warning signal indicates that the position of the patient in space may have changed, such that actions which require the patient's position in space to be known may no longer be taken correctly. The movement warning signal may thus trigger to ascertain the patient's position in space again.

In one embodiment, the steps of acquiring image data and tracking at least one tracked point in the image data are repeated after the movement warning signal has been output. If the patient has moved in space, the relative position between a patient and the thermographic camera has changed. This means that the trajectory may no longer represent the movement of the tracked point on the surface of the patient. In this case, a new trajectory is determined from a new sequence of training thermal images.

In one embodiment, the method further comprises the steps of determining the speed of the tracked point from at least two consecutive live thermal images captured by the thermographic camera, comparing the determined speed with the speed of the tracked point at a corresponding position of the trajectory and outputting a speed warning if the difference of the speeds is above a predetermined threshold. The speed can for example be calculated from the distance between two positions of the tracked point in two consecutive live thermal images. This distance represents the speed of the tracked point, in particular if the time which lies between capturing of the two consecutive live thermal images is known.

The duration of a breathing cycle is typically between 3 and 6 seconds. Within a certain period of time, such as for example several minutes, the duration of the breathing cycle is typically constant. So if the speed of the tracked point determined from the live thermal images significantly differs from the speed derived from the training thermal images, this might be an indication of an abnormal condition of the patient.

Instead of the speed, an acceleration can be used. This means that the acceleration of the tracked point is determined from consecutive live thermal images, the determined acceleration is compared with the acceleration of the tracked point at a corresponding position of the trajectory and an acceleration warning is output if the difference of the accelerations is above a predetermined threshold. The acceleration of the tracked point is for example determined from three consecutive live thermal images. In one implementation, a first speed of the tracked point is determined from the first and second consecutive live thermal images and a second speed is determined from the second and third live thermal images. The acceleration is then determined from the first and second speeds.

In one embodiment, the speed or acceleration of the tracked point is not compared to a speed or acceleration, respectively, at a corresponding point of the trajectory, but with a statistical margin. The statistical margin is for example obtained by averaging the speed or the acceleration over the training thermal images, over a breathing cycle or over a part of the breathing cycle and then a standard deviation is calculated. The statistical margin is then calculated as the standard deviation, optionally multiplied by a factor which is preferably larger than 1, around the average of the speed or acceleration. In another embodiment, the minimum and the maximum of the speed or acceleration is determined and the statistical margin is the range from the minimum to the maximum, optionally broadened by a factor which is larger than 1. This means that the minimum is divided by the factor and the maximum is multiplied by the factor.

In one embodiment, the decision whether a normal breathing takes place or an abnormity, such as abnormal breathing or an additional movement, occurs is made by applying a classificator. The classificator, also referred to as classification, thus decides whether the current state of the patient is normal or not. For this purpose, the classificator is trained at least with the training thermal images. Training of the classificator may continue with the live thermal images. Since the classificator assigns one of two possible states (also referred to as classes), there is a decision boundary between those two states.

In one embodiment, the method further comprises a step of a dimension reduction of the trajectory into one dimension. As explained above, the trajectory is typically a two-dimensional curve in the co-ordinate system of the thermal image. For some applications, it is sufficient to plot the breathing cycle over time, which typically results in a sinosoidal graph. The dimension reduction for example transforms the trajectory, including how the trajectory is traversed over time, into a one-dimensional graph over time.

In one implementation, the dimension reduction step includes determining a main axis of the trajectory and projecting a trajectory onto the main axis. The main axis is for example the line which connects the two points on the trajectory which have the largest possible distance. The length of this line then defines the maximum amplitude of the one-dimensional graph over time. The graph can then be obtained by traversing the trajectory or the positions of the tracked point in the sequence of the training thermal images and projecting the respective points onto the main axis.

As outlined above, one advantage of using thermal images is that points on the surface of a patient can be reliably detected irrespective of exterior conditions such as the illumination in the visible spectrum. There are several approaches for finding the tracked point, that is the same point on the surface of the patient, in a plurality of images, such as the sequence of the training thermal images and any live thermal image. One approach is to assign a particular temperature to the tracked point and to find a point in a thermal image which has the same temperature. A more complex approach is to not only consider the temperature of the tracked point itself, but a thermal signature of an area surrounding the tracked point.

In one embodiment, the method comprises the step of assigning a descriptor to a point on the surface of the patient's body, such as the tracked point. A descriptor is for example a value which is calculated from the properties of the point and optionally also from the properties of points in the vicinity of the point. A descriptor is typically used to unambiguously identify a point. In this document, a descriptor can also be a set of descriptors or descriptor values. A descriptor is for example calculated from a thermal image, for example from the properties of a pixel which represents the point on the surface and/or from the properties of pixels in the vicinity of this pixel.

One advantage of the descriptor is that it is basically invariant over time (such as for example for 1 second, 2 seconds, 5 seconds, 10 seconds, 15 seconds, 30 seconds, 60 seconds or even longer). This means that the descriptor can advantageously be used to identify pixels which show the same point on the surface of the body in the thermal images taken at different points in time.

The principles of calculating a descriptor are for example disclosed in M. Calonder, V. Lepetit, M. Özuysal, T. Trzcinski, C. Strecha, P. Fua, "BRIEF: Computing a Local Binary Descriptor Very Fast", IEEE Transactions on Pattern Analysis and Machine Intelligence, Volume 34, issue No. 07, July 2012, pages 1281 to 1298, which is incorporated by this reference.

Another approach utilizes a neighborhood around a point. This neighborhood in one thermal image is used to define and analyze a similarity function in a so-called integration window in another thermal image. A point which is centered in an integration window in the other thermal image such that is has a neighborhood which is most similar to the neighborhood in the one thermal image is considered to be the same point in the other thermal image. The so-called Lukas-Kanade algorithm provides an effective implementation of this approach.

In one embodiment, the tracked point is selected automatically. For example, a point on the surface is selected as the tracked point if it can be unambiguously identified in the sequence of training thermal images. This means that a point that can be tracked over the whole sequence of training thermal images is automatically selected as the tracked point.

In one implementation, a tracked point is selected automatically within a user-defined area of the thermal image. The user-defined area for example denotes a particular anatomic area, such as the chest or the belly. Those exemplary areas are known to perform a movement which strongly correlates to the breathing action of a patient. So if a tracked point is located within a user-defined are, it can be assumed that the movement of the tracked point represents the breathing action.

In one embodiment, a plurality of tracked points is tracked in the sequence of training thermal images to find trajectories of each of the tracked points. This makes the method more robust, for example towards noise or other inaccuracies when tracking a tracked point in the image data.

As explained above, a trajectory can be a best-fit curve which is fitted into the positions of a tracked point in the image data. Due to inaccuracies in determining the position of the tracked point in a thermal image, the trajectories of different tracked points which are close to each other on the surface of the patient might lead to slightly differing shapes of the trajectories for the tracked points. This can for example be remedied by averaging the trajectories of two or more (neighboring) tracked points on the surface of the patient, in particular of a plurality of point in the same region of the surface. The averaged trajectory can then be assigned to each of the tracked points whose trajectories have been averaged.

In one embodiment, the plurality of tracked points comprises only tracked points with similar main axes of their trajectories. As outlined above, the trajectories typically have an oval shape, wherein each oval has a main axis, which is a line connecting the vertices of the oval. As explained above, the vertices are those two points on the trajectory which have the largest possible distance. Tracked points with similar main axes of their trajectories therefore perform a similar movement during the breathing cycle. It might therefore be advantageous to for example only average those trajectories with similar main axes. In this context, the word "similar" means that the angle between the main axes lies within a limited region, such as within 1°, 2°, 3°, 5° or 1°.

In one modification of or addition to this embodiment, the plurality of tracked points comprises only tracked points with similar phases. The phase of a trajectory is for example defined by the time difference between a reference point in time and a point in time at which a particular point on the trajectory is traversed, such as one of the vertices of the trajectory. A phase is for example similar if the difference between those times is less than 0.1 seconds, 0.2 seconds, 0.3 seconds or 0.5 seconds. In an alternative, the phases are considered similar if those times are below a defined fraction of the duration of a breathing cycle, such as 2%, 5% or 10% of the duration of the breathing cycle.

In one embodiment, the method further comprises the steps of defining a gating region for each tracked point in a live thermal image captured by the thermographic camera, finding the positions of the tracked points in the live thermal image and generating a gating signal indicating whether or not all or the majority of the tracked points are/is within their respective gating region. This embodiment is similar to the embodiment where a single gating region is defined for a single tracked point. However, in this embodiment, independent gating regions can be defined for the tracked points. In one implementation, the gating signals indicates that all of the tracked points are within their respective gating regions in the (same) live thermal image, which means that the tracked points are at defined positions of the trajectory at the same point in time. In another implementation, it is sufficient that the majority of the tracked points is within their respective gating regions. Potential phase differences between the trajectories of the tracked points can be compensated by appropriately defining the gating regions. This means that the gating regions do not necessarily have for example to be at the same vertex of the trajectories.

In this embodiment, the expression "majority" means a particular fraction out of all the tracked points, such as for example 80%, 90%, 95%, 98% or 99% of all tracked points.

This embodiment makes the generation of the gating signal more robust. If the positions of a minority of the tracked points cannot be correctly determined, for example due to noise in the live thermal image, a correct gating signal can be generated anyway.

In one embodiment, the method further comprises the steps of determining a main axis of the trajectory of each of the tracked points, projecting the trajectories into the respective main axis and averaging the projected trajectories to obtain one-dimensional breathing signal data. This embodiment is similar to the embodiment in which the main axis of the trajectory of a single tracked point is determined and the trajectory or the positions of the single tracked point is/are projected onto the main axis. However, in the present embodiment, a plurality of projected trajectories of a plurality of tracked points is averaged, such that the one-dimensional breathing signal data is more reliable.

In one embodiment, the method further comprises the step of correlating the trajectory to a movement of a tumor as described by a tumor movement model.

A tumor is typically not at a fixed position within the patient's body, but can move, for example due to a breathing action of the patient. Tumor movement models which describe the movement of a tumor due to a breathing action are known. If the trajectory of a tracked point is correlated to the movement of a tumor as described by a tumor movement model, the position of the tumor can be calculated from the position of the tracked point on the trajectory. The breathing signal data is then a surrogate for a tumor movement signal which describes the movement of the tumor within a patient's body.

In one embodiment, the imaged (part of) the surface of the patient's body is divided into two or more areas and a trajectory of at least one point in each of the areas is determined as explained above. This means that there is at least one trajectory in each of the areas. In one implementation, one or more averaged trajectories can be calculated for each of the areas from the trajectories in those areas, in particular by averaging the trajectories in the same area. This is particularly useful if the surface points in each of the areas have identical or similar trajectories, while the trajectories of surface points of different areas differ from each other.

In one embodiment, the method further comprises the steps of determining the direction of the tracked point from at least two consecutive live thermal images captured by the thermographic camera, comparing the determined direction with the direction of the tracked point at a corresponding position of the trajectory and outputting a direction warning if the difference of the directions is above a predetermined threshold. The predetermined threshold is for example 5°, 10°, 20°, 30°, 45° or 60°. In this embodiment, a deviation of the tracked point from its trajectory can be determined, for example even before the position of the tracked point is outside of a corridor or an area around the trajectory.

An advantage of the present invention is that it does not need any calibration procedure before the breathing signal data can be determined. In addition, a single thermographic camera, in particular a single two-dimensional thermographic camera, is sufficient to determine the breathing signal data. In addition, a tracked point on the surface of the patient can be tracked with a high frequency according to the frame rate of the thermographic camera, which is typically between 30 hz and 60 hz or even higher.

The present invention also relates to a computer program embodied on a non-transitory computer-readable medium which, when running on a computer or loaded onto a computer, causes the computer to perform any one or more of the data processing methods described above.

The present invention further relates to a system for determining breathing signal data which represents a breathing cycle of a patient, comprising a computer on which the aforementioned program is stored and/or run.

The invention does for example relate to the Applicant's product ExacTrac® which is used for patient setup and monitoring in radiotherapy. The invention can be used for calculating a gating signal for gating a treatment beam or for calculating a movement signal which represents the movement of a structure, such as a tumour, for controlling the direction of a treatment beam. It can further be used for any other application that makes use of a breathing signal, such as the Applicant's Vero® system.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

A treatment beam treats body parts which are to be treated and which are referred to in the following as "treatment body parts". These body parts are for example parts of a patient's body, i.e. anatomical body parts.

The present invention relates to the field of medicine and for example to enable the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: www.elekta.com/healthcare_us_elekta_vmat.php and www.varian.com/us/oncology/treatments/treatment_techniques/rapidarc.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

In the following, the invention is described with reference to the enclosed figures which represent preferred embodiments of the invention. The scope of the invention is not however limited to the specific features disclosed in the figures, which show:

FIG. 1 a schematic representation of a system according to the invention;

FIG. 2 a sequence of training thermal images;

FIG. 3*a* a superimposed image of the positions of a tracked point in the sequence of training thermal images;

FIG. 3*b* a trajectory determined from the positions shown in FIG. 3*a*;

FIG. 4 a flow diagram of determining a trajectory of a tracked point;

FIG. 5 an image showing a gating region;

FIG. 6 a flow diagram of gating a treatment beam;

FIG. 7 an image comprising a corridor around the trajectory;

FIG. 8 a flow diagram of outputting a movement warning signal;

FIG. 9 an image showing the main axis of the trajectory;

FIG. 10 a graph showing the projection of the trajectory onto the main axis over time; and FIG. 11 an image comprising two regions and a plurality of trajectories.

FIG. 1 shows a system 1 for determining breathing signal data which represents a breathing cycle of a patient P. The system 1 comprises a computer 2 connected to a thermographic camera 3, an input device 10 and an output device 11.

The thermographic camera 3 comprises a thermographic imaging unit 4. The imaging unit 4 comprises a lens system 5 and a sensor 6. The lens system 5 guides incident thermal radiation onto the sensor 6, wherein the sensor 6 generates a two-dimensional thermal image which preferably represents wavelengths of between 8 µm and 14 µm. The lens system 5 has a characteristic axis similar to the optical axis of a camera which captures an image in the visible spectrum. The characteristic axis is shown as a dashed line in FIG. 1.

Thermal radiation emitted from a point on the body is guided onto one or more pixels of the sensor 6 in accordance with the spatial location of the point on the surface of the patient's body and the characteristics of the lens system 5.

In the present example, the sensor 6 is a two-dimensional array of sensor cells which convert incident thermal radiation into a voltage which corresponds to the temperature of the corresponding point on the surface of the patient's body.

The temperature is typically derived from the wavelength of the maximum within the spectrum of the incident infrared radiation.

The thermographic camera 3 is arranged in a fixed spatial position, for example in an operation theater. The patient P does for example lie on an operation couch.

The computer 2 comprises a central processing unit 7, a memory unit 8 and an interface 9. The memory unit 8 stores program data and/or working data, such as the image data acquired from the thermographic camera 3. The computer is connected to the input device 10, the output device 11 and/or the thermographic camera 3 via the interface 9.

The computer 2 acquires the image data, which represents a sequence of two-dimensional training thermal images which were captured using the sensor 6, from the thermographic camera 3. The computer 2 determines the pixels in the two-dimensional training thermal images which show the thermal radiation emitted from the same point, which is a tracked point, on the surface of the patient's body. The pixels are for example determined by means of a descriptor which describes the thermal signature of the tracked point and the area surrounding this point, such that the descriptor is characteristic of this point.

FIG. 2 shows some training thermal images T1, T2, T3 and TN out of the sequence of N training thermal images. In each of the training thermal images T1-TN, the position at which the tracked point TP is imaged is shown by a dot. The tracked point TP is identified and located in the training thermal images by means of known algorithms. The sequence of training thermal images T was captured by the thermographic camera 3 over a full breathing cycle of the patient P.

FIG. 3a shows an image on which the positions of the tracked point TP in the sequence of training thermal images are superimposed. The positions form a set of positions. Shown in FIG. 3b is the set of positions of FIG. 3a together with a trajectory T which is a best-fit curve for the set of positions. The trajectory T is not only a curve which represents the positions of the tracked point in the training thermal images, but also has a temporal component which represents a time at which the tracked point is at a particular position. The direction in which the trajectory T is traversed during a breathing cycle of the patient P is indicated by an arrow.

FIG. 4 is a flow diagram of a process for determining breathing signal data. Step S01 involves inquiring image data from the thermographic camera 3 by the computer 2. The image data comprises a sequence of training thermal images of at least a part of the surface of the patient's body over time, such as the sequence of training thermal images T1-TN of FIG. 2. The image data is stored in the memory 8.

Step S02 involves identifying a point of the surface of the patient's body which is to be tracked in the sequence of training thermal images, which means that a tracked point is identified. In other words, a suitable point is found, in particular a point which can be reliably tracked in the sequence of training thermal images, for example due to its thermal signature.

Step S03 involves determining metadata of the tracked point. The metadata describe properties of the tracked point which can be used to find the tracked point in the sequence of training thermal images. The metadata can for example be a temperature of the tracked point, a thermal signature of the tracked point or of an area around the tracked point including the tracked point, or a descriptor of the tracked point.

Step S04 involves tracking the tracked point in the sequence of training thermal images. This means that the position of the tracked point is determined in each of the training thermal images, for example by using the metadata of the tracked point. FIG. 2 shows the positions of the tracked point in the sequence of training thermal images T1-TN.

Step S05 involves finding a trajectory of the tracked point from the positions of the tracked point in the sequence of training thermal images. This step for example comprises to fit a curve into the set of positions of the tracked point in the training thermal images. For the set of positions of the tracked point as shown in FIG. 3a, the trajectory T as shown in FIG. 3b is found. The trajectory describes the movement of the tracked point in the training thermal images over a breathing cycle of the patient P, and therefore is breathing signal data which represents a breathing cycle of the patient. The positions of the tracked point in the sequence of training thermal images and/or the trajectory are displayed on the output device 11.

Steps S02 to S05 are in particular carried out by the central processing unit 7 of the computer 2.

Figure 1:
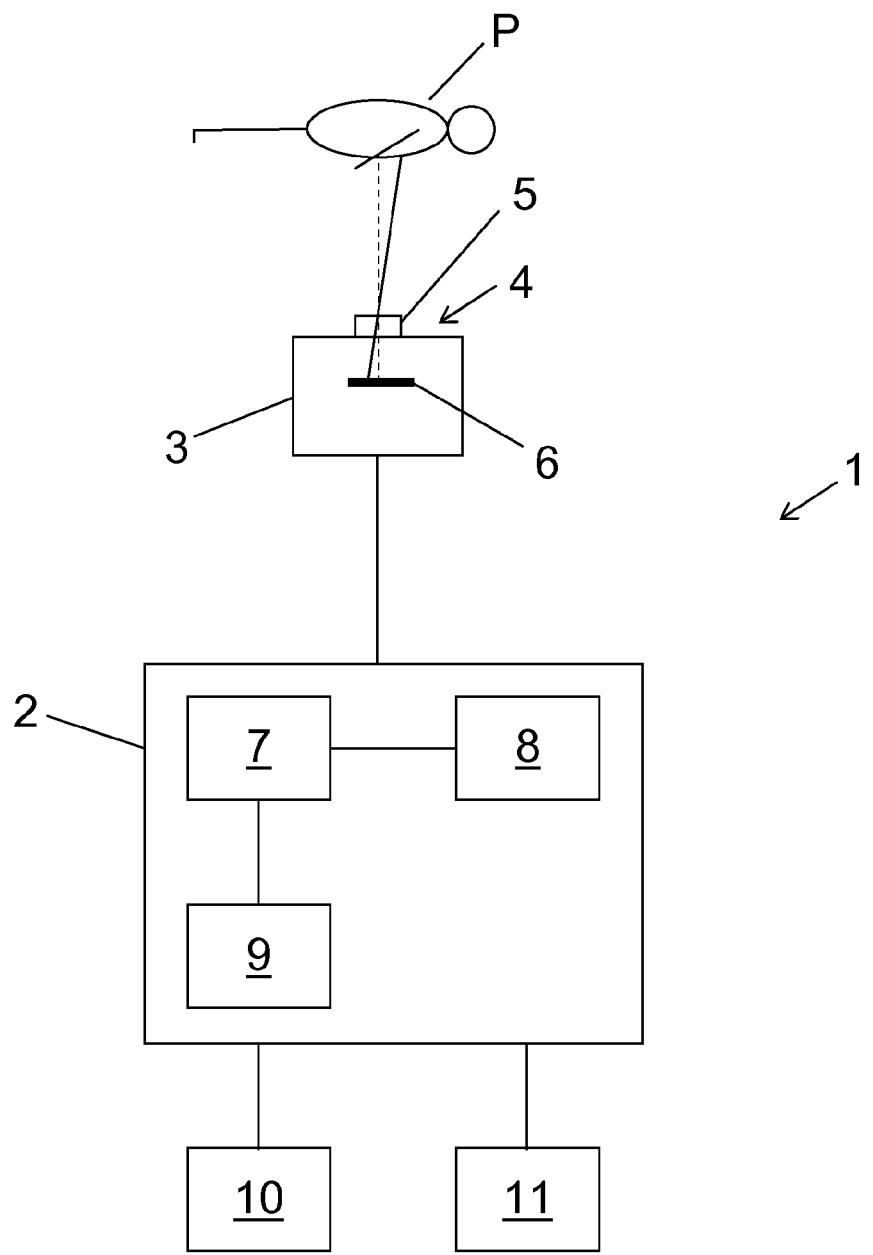
Figure 2:
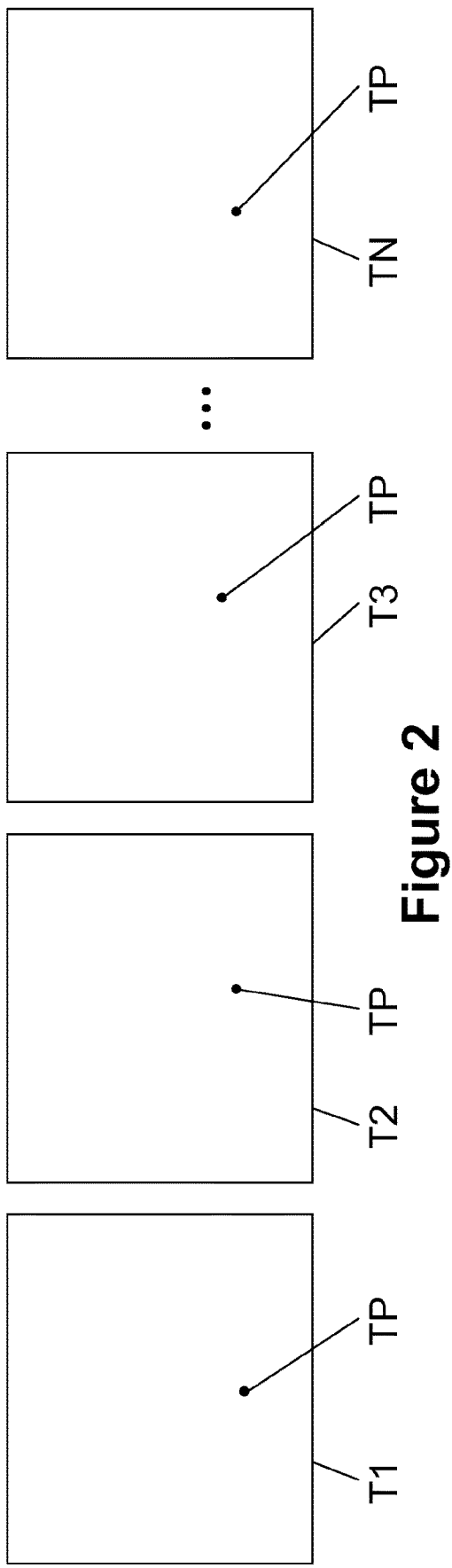
Figure 3B:
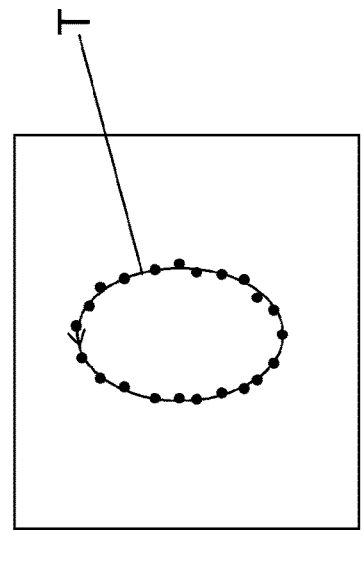
Figure 3A:
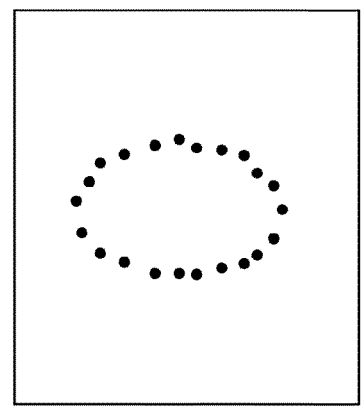
Figure 4:
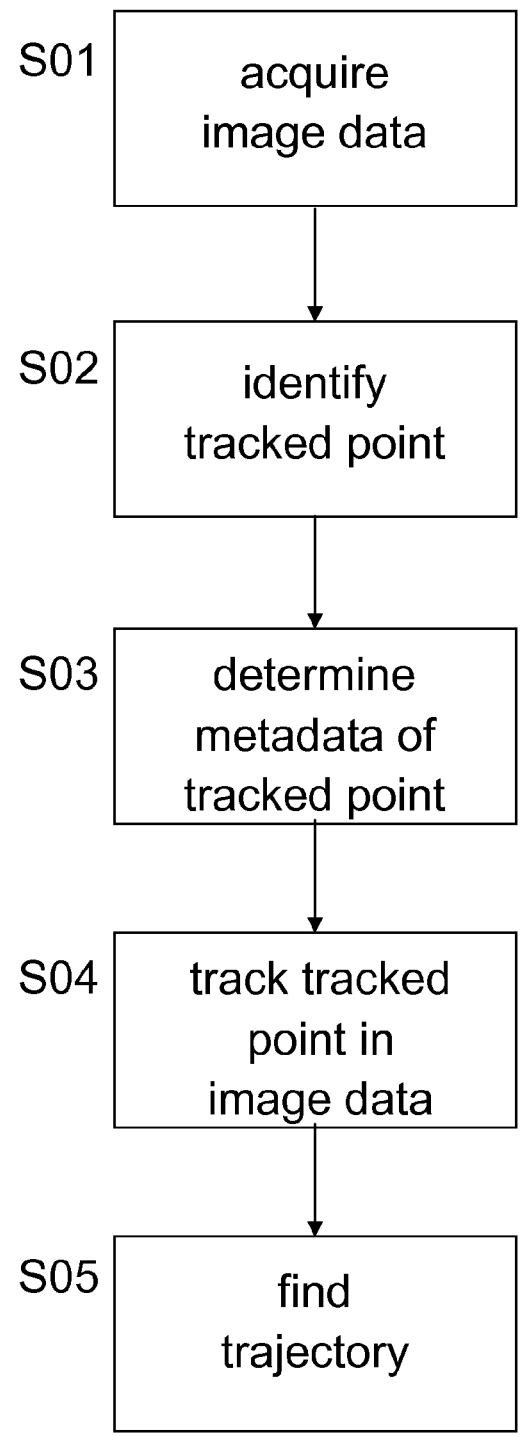
Figure 5:
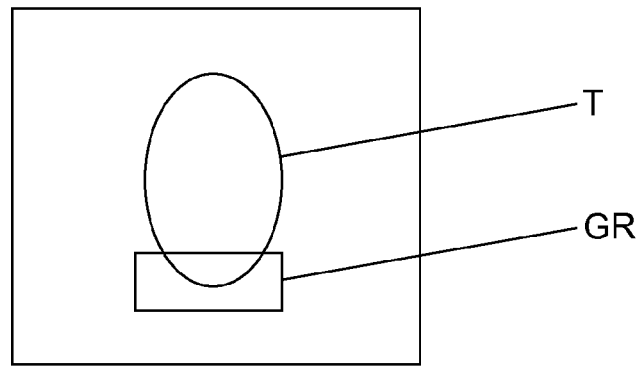
FIG. 5 shows an image with the trajectory T and a gating region GR, which in the present example is a rectangular area which comprises a part of a trajectory T including the lower vertex of the trajectory T.

In step S11, a gating region is defined, such as the gating region GR in FIG. 5. In general, the gating region comprises a part of the trajectory. The gating region is for example input by a user using the input device 10.

In step S12, a live thermal image is acquired by the thermographic camera 3. The point in time at which the live thermal image is acquired is after the point in time at which the last image of the sequence of training thermal images was captured.

In step S13, the position of the tracked point is determined in the live thermal image. Step S13 for example uses the metadata of the tracked point determined in step S03.

In step S14, it is determined whether or not the position of the tracked point in the live thermal image lies within the gating region, such as the gating region GR of FIG. 5. If the position of the tracked point is outside the gating region (no in step S14), a gating signal indicating that the treatment beam is to be turned off is generated in step S15 and the process returns to step S12. If it is determined that the position of the tracked point is within the gating region (yes in step S14), a gating signal indicating that the treatment beam is to be switched on is generated in step S16 and the process proceeds to step S12.

Figure 6:
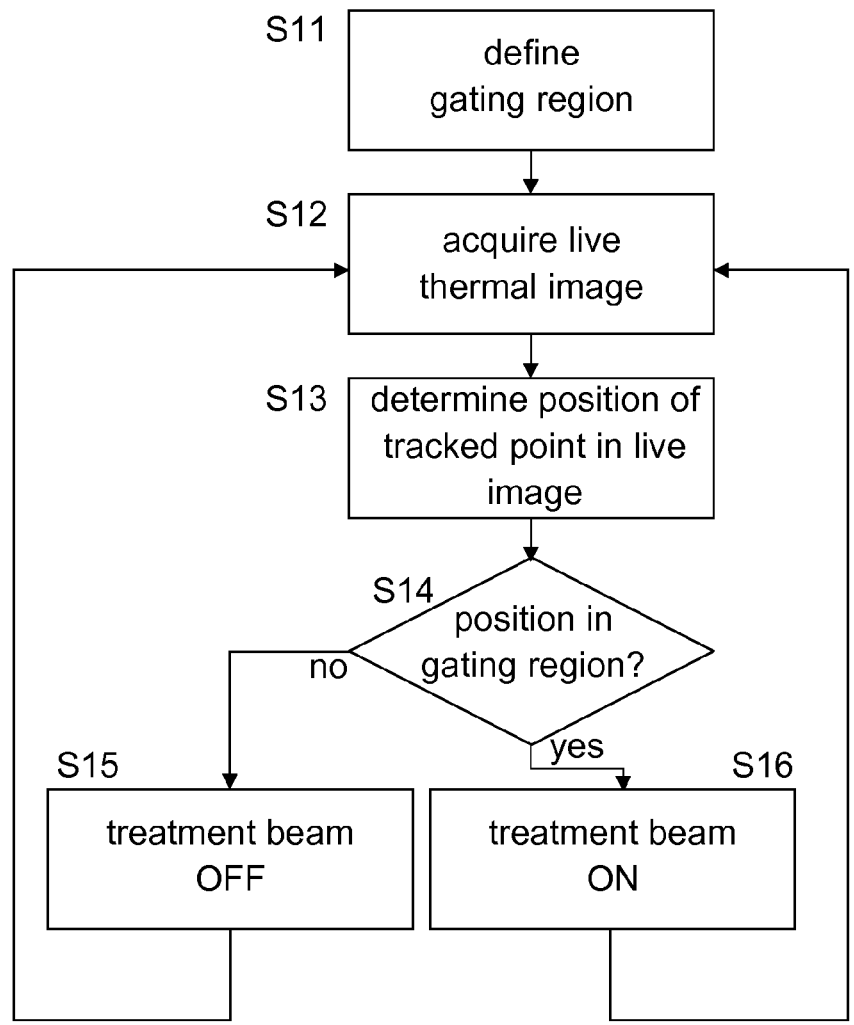
FIG. 6 shows a flow diagram of a process for generating a gating signal which can be used for turning a treatment beam on and off. The process is performed subsequent to step S05 of the flow diagram shown in FIG. 4.

In the process shown in FIG. 6, it is continuously determined whether or not the position of the tracked point is within the gating region, which means that the current state of the patient's breathing action is in a defined part of the breathing cycle. The gating signal can then be generating accordingly, such that the treatment beam is switched on only during a certain phase of the breathing cycle.

Figure 7:
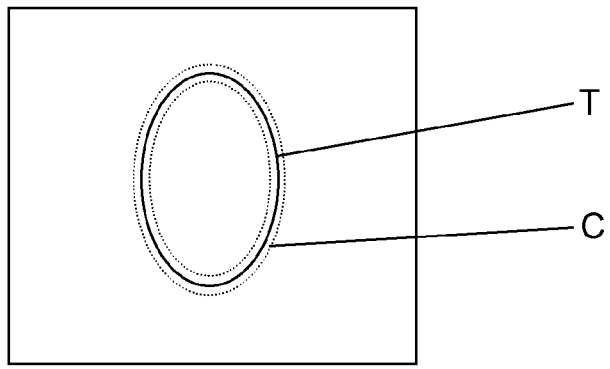

FIG. 7 shows an image with the trajectory T and a corridor C around the trajectory T, wherein the corridor C is indicated by dotted lines. The corridor C is a two-dimensional area around the trajectory T in the image.

Figure 8:
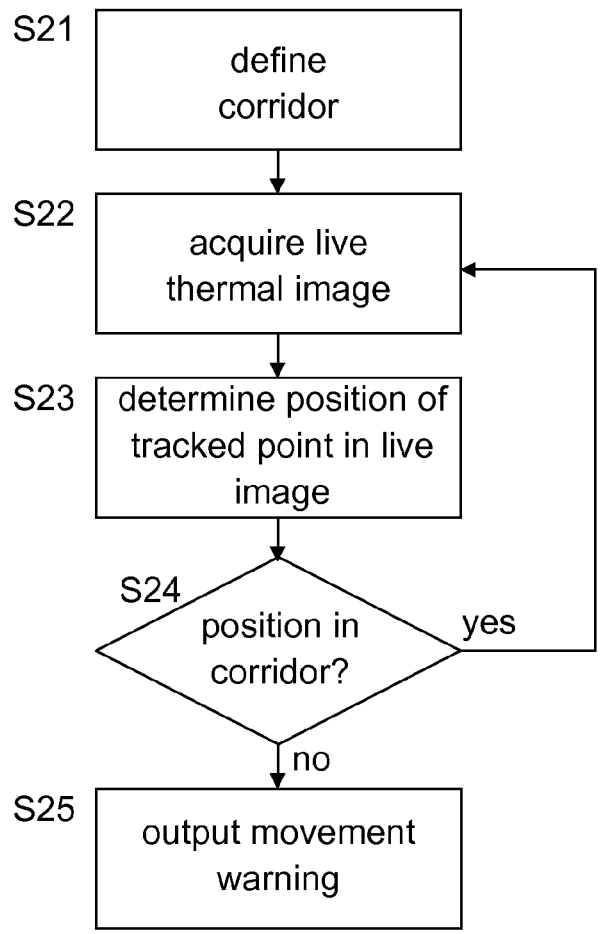

FIG. 8 shows a flow diagram of a process for outputting a movement warning which is carried out subsequent to the step S05.

In step S21, a corridor around the trajectory is defined, such as the corridor C around the trajectory T as shown in FIG. 7.

In step S22, a live thermal image is acquired like in step S12, and in step S23 the position of the tracked point in the live thermal image is determined like in step S13, such that repeating details of those steps is omitted.

In step S24, it is determined whether or not the position of the tracked point determined in step S23 lies within the corridor, such as the corridor C in FIG. 7. If the position does not lie within the corridor (no in step S24), a movement warning is output in step S25. If the position of the tracked point lies within the corridor (yes in step S24), the process returns to step S22.

The corridor defined around the trajectory defines a margin by which the position of the tracked point may deviate from the trajectory, which might be a best-fit curve, without being considered as being abnormal. If the position of the tracked point deviates by more than the margin as defined by the corridor, the position of the tracked point is considered to be abnormal, which might for example be caused by a movement of the patient other than a movement caused by the breathing action.

Figure 9:
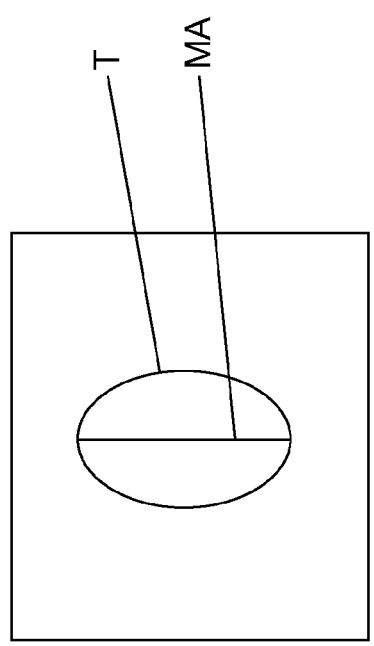

FIG. 9 shows an image in which a main axis MA of the trajectory T is drawn. The main axis MA is the line which connects the two points on the trajectory T which have the largest possible distance. Since the exemplary trajectory T is an oval, the main axis is the long axis of symmetry of the oval.

Figure 10:
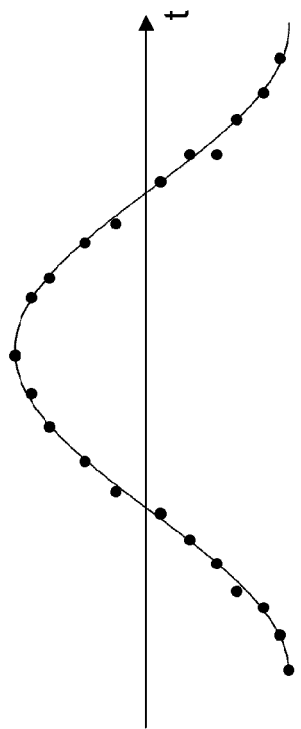

As explained above, the trajectory T is determined from the positions of the tracked point over time. FIG. 10 shows the orthogonal projections of the positions of the tracked point onto the main axis MA over time. FIG. 10 further shows a continuous curve which is the best-fit curve for the projections of the positions of the tracked point onto the main axis MA over time. This curve is sinusoidal and represents a principle component of the movement of the tracked point in the training thermal images. In order to monitor the breathing activity of the patient P, the position of the tracked point in live thermal image is determined and projected onto the main axis MA, such that the actual breathing activity can be plotted over time in real-time.

Figure 11:
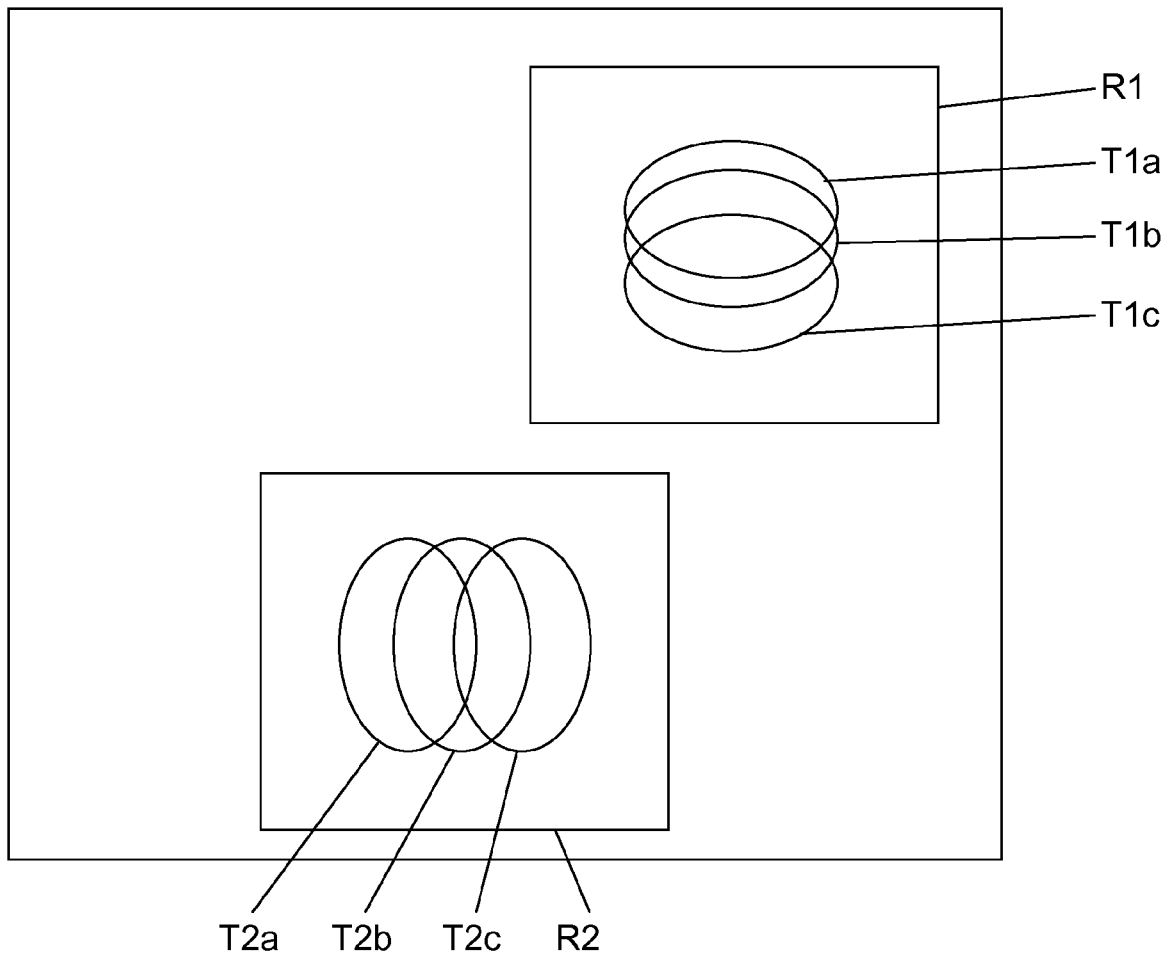

FIG. 11 shows an image in which two areas or regions R1 and R2 are defined. In the region R1, the trajectories T1a, T1b and T1c of tracked points TP1a, TP1b and TP1c (not shown) are depicted. In the region R2, the trajectories T2a, T2b and T2c of tracked points TP2a, TP2b and TP2c are shown. As can be seen from FIG. 11, the trajectories T1a, T1b and T1c have a very similar or even identical shape, and are only shifted relative to each other because the tracked points TP1a, TP1b and TP1c are offset relative to each other on the surface of the patient P. In analogy, the shape of the trajectories T2a, T2b and T2c is similar or even identical, but those trajectories are offset relative to each other since the tracked points TP2a, TP2b and TP2c are offset relative to each other on the surface of the patient P.

It can further be seen that the trajectories in the region R1 are different from the trajectories in the region R2. The reason for this might be that different regions of the surface of the patient's body perform different movements due to the breathing activity. The region R1 might for example represent the chest, while the region R2 represents the abdomen.

The similarity of the movement of the tracked points within the respective regions R1 and R2 can be used to make the determination of the breathing signal data more robust. In one embodiment, the trajectories within each region can be averaged and be assigned to all tracked points within the respective region. In another embodiment, a gating region or a corridor can be assigned to each of the trajectories within a region and a warning signal, such as a movement warning signal, a speed warning signal or a gating signal can be generated by accounting for each of the trajectories within a region. So for example each or a predetermined fraction of tracked points within a region have to lie within the corresponding gating region in a live thermal image in order to generate a gating signal indicating that the treatment beam is to be turned on. In another example, each or a predetermined fraction of the tracked points in a region have to lie within the corresponding corridor in order to determine that no movement warning signal is to be output.

In another example, the main axis of each trajectory within a region are determined and averaged and the positions of the tracked points are projected onto the average main axis in order to obtain a one-dimensional breathing signal over time.

In FIGS. 2, 3a, 3b, 5, 7, 9 and 11, the positions of the tracked point and/or the trajectory are given with respect to the co-ordinate system of the image. This co-ordinate system corresponds to the sensor 6. The positions of the tracked point in the thermal images is defined by the projection of the tracked point from its position in space into the image plaine of the sensor 6 depending on the properties of the thermographic camera 3, and in particular on the characteristics of the lens system 5. Since the thermographic camera 3 is considered to be fixed in space, the co-ordinate systems of the images shown in FIGS. 2, 3a, 3b, 5, 7, 9 and 11 are considered to be congruent.

The invention claimed is:

1. A method implemented by a computer having one or more processors, comprising:
    acquiring image data representing a sequence of training thermal images of at least a part of a surface of a patient's body over time, the sequence covering at least one half breathing cycle and being captured by a thermographic camera;
    tracking at least one tracked point in the image data over the sequence of training thermal images to find a trajectory of the at least one tracked point as breathing signal data, wherein the at least one tracked point is a point on the surface of the patient's body; and
    defining a gating region in a live thermal image captured by the thermographic camera, wherein the gating region is an area of the live thermal image and wherein at least a part of the trajectory lies in the gating region;
    finding a position of the at least one tracked point in the live thermal image; and
    generating a gating signal indicating whether or not the at least one tracked point is within the gating region.

2. The method of claim 1, further comprising the steps of defining a corridor around the trajectory in a live thermal image captured by the thermographic camera, finding the position of the at least one tracked point in the live thermal image and outputting a movement warning signal if the position of the at least one tracked point is outside the corridor.

3. The method of claim 1, further comprising the steps of determining the speed of the at least one tracked point from at least two consecutive live thermal images captured by the thermographic camera, comparing the determined speed with the speed of the at least one tracked point at a corresponding position of the trajectory and outputting a speed warning if the difference of the speeds is above a predetermined threshold.

4. The method of claim 1, further comprising a step of a dimension reduction of the trajectory into one dimension.

5. The method of claim 4, wherein the dimension reduction step includes determining a main axis of the trajectory and projecting the trajectory onto the main axis.

6. The method of claim 1, wherein the at least one tracked point is selected automatically.

7. The method of claim 6, wherein the at least one tracked point is selected automatically within a user-defined area of the thermal image.

8. The method of claim 1, wherein a plurality of tracked points are tracked in the sequence of training thermal images to find trajectories of each of the tracked points.

9. The method of claim 8, wherein the plurality of tracked points comprises only tracked points with similar main axes of their trajectories.

10. The method of claim 8, further comprising the steps of defining a gating region for each of the plurality of tracked points in a live thermal image captured by the thermographic camera, finding the positions of each of the tracked points in the live thermal image and generating a gating signal indicating whether or not all or the majority of the tracked points are within their respective gating region.

11. The method of claim 8, further comprising the steps of determining a main axis of the trajectory of each of the tracked points, projecting the trajectories onto the respective main axis and averaging the projected trajectories to obtain one-dimensional breathing signal data.

12. The method of claim 1, further comprising the step of correlating the trajectory to a movement of a tumour as described by a tumour movement model.

13. A non-transitory computer readable storage medium comprising stored instructions executable by at least one processor to:
- acquire image data representing a sequence of training thermal images of at least a part of the surface of the patient's body over time, the sequence covering at least one half breathing cycle and being captured by a thermographic camera;
- track at least one tracked point in the image data over the sequence of training thermal images to find a trajectory of the at least one tracked point as the breathing signal data, wherein the at least one tracked point is a point on the surface of the patient's body; and
- define a gating region in a live thermal image captured by the thermographic camera, wherein the gating region is an area of the live thermal image and wherein at least a part of the trajectory lies in the gating region;
- find a position of the at least one tracked point in the live thermal image; and
- generate a gating signal indicating whether or not the at least one tracked point is within the gating region.

14. A system including memory and one or more processors operable to execute instructions stored in the memory, comprising instructions to:
- acquire image data representing a sequence of training thermal images of at least a part of the surface of the patient's body over time, the sequence covering at least one half breathing cycle and being captured by a thermographic camera;
- track at least one tracked point in the image data over the sequence of training thermal images to find a trajectory of the at least one tracked point as the breathing signal data, wherein the at least one tracked point is a point on the surface of the patient's body; and
- define a gating region in a live thermal image captured by the thermographic camera, wherein the gating region is an area of the live thermal image and wherein at least a part of the trajectory lies in the gating region;
- find a position of the at least one tracked point in the live thermal image; and
- generate a gating signal indicating whether or not the at least one tracked point is within the gating region.

* * * * *